United States Patent [19]

St. Georgiev et al.

[11] Patent Number: 4,803,282

[45] Date of Patent: Feb. 7, 1989

[54] ALPHA-SUBSTITUTED KETONITRONE DERIVATIVES

[75] Inventors: Vassil St. Georgiev, Rochester; George B. Mullen, Avon, both of N.Y.

[73] Assignee: Pennwalt Corporation, Philadelphia, Pa.

[21] Appl. No.: 900,856

[22] Filed: Aug. 27, 1986

[51] Int. Cl.[4] .................. C07D 409/06; C07D 405/06; C07D 233/61
[52] U.S. Cl. ................................ 548/336; 548/262; 548/341
[58] Field of Search ................................ 548/341, 336

[56] References Cited

U.S. PATENT DOCUMENTS 4,719,306  1/1988  St. Georgiev et al. ............. 548/240

OTHER PUBLICATIONS

Tutariello, Joseph J., "Nitrones", Chapter 9, 1,3 *Dipolar Cycloaddition Chemistry*, vol. 2, (Ed. A. Padwa). pp. 83–97 and 153–157, John Wiley, New York, 1984.

Primary Examiner—Richard A. Schwartz

[57] ABSTRACT

α-Substituted ketonitrone derivatives containing substitutents selected from hydrogen, phenyl, substituted phenyl, naphythyl, furan, thiopen, imidazolylmethyl and triazolylmethyl are useful as intermediates for the preparation of biologically active isoxazolidine compounds.

18 Claims, No Drawings

ALPHA-SUBSTITUTED KETONITRONE DERIVATIVES

BACKGROUND OF THE INVENTION

This invention relates to α-substituted ketonitrone derivatives useful as intermediates for the preparation of antifungal isoxazolidine compounds.

BRIEF SUMMARY OF THE INVENTION

In accordance with this invention there are provided compounds of the formula:

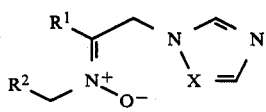

wherein;

$R^1$ is selected from 2-naphthyl, 2-furanyl, 2-thienyl, phenyl, and substituted phenyl having one or more of the meta and para hydrogens substituted by halogen, lower alkoxy, lower alkyl or combinations thereof, $R^2$ is selected from hydrogen and phenyl, and X is selected from nitrogen and a methyn (CH=) group.

DETAILED DESCRIPTION OF THE INVENTION

The α-substituted ketonitrone derivatives (2) of the invention can be obtained as illustrated in the following diagram by reaction of an appropriately substituted ketone precursor (1) with N-methyl(or benzyl)-hydroxylamine hydrochloride in absolute ethanol at room or elevated temperature in the presence of base, for example, alkali metal carbonates, bicarbonates or acetates. Preferably, potassium carbonate or sodium acetate are used.

As used herein the terms "lower alkyl" and "lower alkoxy" refer to straight and branched chain alkylene groups having 1 to 4 carbon atoms and halogen refers to chlorine, bromine, iodine and fluorine (preferably chlorine or fluorine).

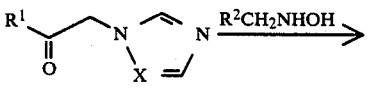

1

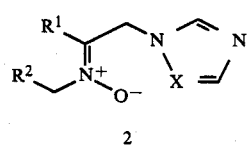

2

The preparation of the compounds of the invention is further illustrated by the following examples. The appropriately substituted ketone precursors are prepared according to known procedures, for example, Godefroi et al., J. Medicinal Chem. 12 784 (1969), and Nardi et al., J. Medicinal Chem. 24 727 (1981).

EXAMPLE 1

2-(1H-Imidazol-1-yl)-N-methyl-1-phenylethanimine N-oxide (2, $R^1 = C_6H_5$, $R^2 = H$, X=CH)

Method A. A suspension of 18.70 g (0.100 mol) of 2-(1H-imidazol-1-yl)acetophenone (1, $R^1 = C_6H_5$, X=CH), N-methylhydroxylamine hydrochloride (9.78 g, 0.117 mol), and potassium carbonate (17.24 g, 0.125 mol) in 200 ml of absolute ethanol was stirred at 70°–75° C., under a nitrogen atmosphere, for 48 hours. The reaction mixture was then cooled to room temperature, filtered, and the solvent removed in vacuo, leaving a yellow oil which was dissolved in 400 ml of ethyl acetate and extracted with water (6×100 ml). The combined aqueous layer was back-extracted with chloroform (8×100 ml). The combined chloroform layer was dried over anhydrous sodium sulfate, filtered, and the solvent removed in vacuo to give nitrone 2 ($R^1 = C_6H_5$, $R^2 = H$, X=CH) as a white solid, 15.54 g (72%). An analytical sample was prepared by recrystallization from ethyl acetate, mp 126°–128° C. Anal. Calcd for $C_{12}H_{13}N_3O$: C, 66.96; H, 6.09; N, 19.52. Found: C, 66.74; H, 6.18; N, 19.38.

Method B. A suspension of 5.58 g (0.0316 mol) of 2-(1H-imidazol-1-yl)acetophenone (1, $R^1 = C_6H_5$, X=CH), N-methylhydroxylamine hydrochloride (3.17 g, 0.0379 mol), and sodium acetate (6.24 g, 0.0760 mol) in 50 ml of absolute ethanol was stirred for 72 hours at room temperature, under a nitrogen atmosphere. The suspension was then filtered and the solvent removed in vacuo. The residual oily solid was taken up in chloroform, filtered and the solvent removed in vacuo. Crystallization from ethyl acetate gave 5.43 g (80%) of nitrone 2 ($R^1 = C_6H_5$, $R^2 = H$, X=CH).

EXAMPLE 2

1-(4-Chlorophenyl)-2-(1H-imidazol-1-yl)-N-methylethanimine N-oxide (2, $R^1 = 4\text{-ClC}_6H_4$, $R^2 = H$, X=CH)

Compound 2 ($R^1 = 4\text{-ClC}_6H_4$, $R^2 = H$, X=CH) was prepared by the procedures described in Example 1, Methods A and B by reacting 2-(1H-imidazol-1-yl)-4'-chloroacetophenone (1, $R^1 = 4\text{-ClC}_6H_4$, X=CH) with N-methylhydroxylamine hydrochloride. Compound 2 ($R^1 = 4\text{-ClC}_6H_4$, $R^2 = H$, X=CH) has a melting point of 98°–102° C. (ethyl acetate). Anal. Calcd for $C_{12}H_{12}ClN_3O$: C, 57.72; H, 4.84; N, 16.83; Cl, 14.20. Found (method A prep): C, 57.53; H, 4.99; N, 16.87; Cl, 14.08.

EXAMPLE 3

1-(4-Fluorophenyl)-2-(1H-imidazol-1-yl)-N-methylethanimine N-oxide (2, $R^1 = 4\text{-FC}_6H_4$, $R^2 = H$, X=CH)

Compound 2 ($R^1 = 4\text{-FC}_6H_4$, $R^2 = H$, X=CH) was prepared by the procedures described in Example 1, Methods A and B, by reacting 2-(1H-imidazol-1-yl)-4'-fluoroacetophenone (1, $R^1 = 4\text{-FC}_6H_4$, X=CH) with N-methylhydroxylamine hydrochloride. Compound 2 ($R^1 = 4\text{-FC}_6H_4$, $R^2 = H$, X=CH) has a melting point of 131°–134° C. (ethyl acetate). Anal. Calcd for $C_{12}H_{12}FN_3O$: C, 61.79; H, 5.19, N, 18.02; F, 8.15. Found (method A prep.): C, 62.02; H, 5.39; N, 17.96; F, 8.22.

EXAMPLE 4

2-(1H-Imidazol-1-yl)-1-(4-methoxyphenyl)-N-methylethanimine N-oxide (2, $R^1$=4-$CH_3OC_6H_4$, $R^2$=H, X=CH)

Compound 2 ($R^1$=4-$CH_3OC_6H_4$, $R^2$=H, X=CH) was prepared by the procedure described in Example 1, Method A, by reacting 2-(1H-imidazol-1-yl)-4'-methoxyacetophenone (1, $R^1$=4-$CH_3OC_6H_4$, X=CH) with N-methylhydroxylamine hydrochloride. Compound 2 ($R^1$=4-$CH_3OC_6H_4$, $R^2$=H, X=CH) has a melting point of 81°–84° C. (ethyl acetate-ether, 1:1 by volume). Anal. Calcd for $C_{13}H_{15}N_3O_2$: C, 63.66; H, 6.16; N, 17.13. Found: C, 63.49; H, 6.28; N, 17.05.

EXAMPLE 5

2-(1H-Imidazol-1-yl)-1-(3-methoxyphenyl)-N-methylethanimine N-oxide (2, $R^2$=3-$CH_3O_6H_4$, $R^2$=H, X=CH)

Compound 2 ($R^1$=3-$CH_3OC_6H_4$, $R^2$=H, X=CH) was prepared by the procedure described in Example 1, Method A, by reacting 2-(1H-imidazol-1-yl)-3'-methoxyacetophenone (1, $R^1$=3-$CH_3OC_6H_4$, X=CH) with N-methylhydroxylamine hydrochloride. Compound 2 ($R^1$=3-$CH_3OC_6H_4$, $R^2$=H, X=CH) has a melting point of 87°–90° C. (ethyl acetate-hexane, 1:1 by volume). Anal. Calcd for $C_{13}H_{15}N_3O_2$: C, 63.66; H, 6.16; N, 17.13. Found: C, 63.70; H, 6.29; N, 17.08.

EXAMPLE 6

2-(1H-Imidazol-1-yl)-N-methyl-1-(3-methylphenyl)ethanimine N-oxide (2, $R^1$=3-$CH_3C_6H_4$, $R^2$=H, X=CH)

Compound 2 ($R^1$=3-$CH_3C_6H_4$, $R^2$=H, X=CH) was prepared by the procedure described in Example 1, Method B, by reacting 2-(1H-imidazol-1-yl)-3'-methylacetophenone (1, $R^1$=3-$CH_3C_6H_4$, X=CH) with N-methylhydroxylamine hydrochloride. Compound 2 ($R^1$=3-$CH_3C_6H_4$, $R^2$=H, X=CH) was obtained as a light yellow oil.

EXAMPLE 7

1-(4-Chloro-3-methylphenyl)-2-(1H-imidazol-1-yl)-N-methylethanimine N-oxide (2, $R^1$=4-Cl-3-$CH_3C_6H_3$, $R^2$=H, X=CH) Compound 2 ($R^1$=4-Cl-3-$CH_3C_6H_3$, $R^2$=H, X=CH) was prepared by the procedure described in Example 1, Method A, by reacting 2-(1H-imidazol-1-yl)-4'-chloro-3'-methylacetophenone (1, $R^1$=4-Cl-3-$CH_3C_6H_3$, X=CH) with N-methylhydroxyamine hydrochloride. Compound 2 ($R^1$=4-Cl-3-$CH_3C_6H_5$, $R^2$=H, X=CH) was obtained as a light yellow oil. EXAMPLE 8

2-(1H-Imidazol-1-yl)-1-phenyl-N-(phenylmethyl)ethanimine N-oxide (2, $R^1$=$R^2$=$C_6H_5$, X=CH)

Compound 2 ($R^1$=$R^2C_6H_5$, X=CH) was prepared by the procedure described in Example 1, Method B, by reacting 2-(1H-imidazol-1-yl)acetophenone (1, $R^1$=$C_6H_5$, X=CH) with N-benzylhydroxylamine. Compound 2 ($R^1$=$R^2$=$C_6H_5$, X=CH) was obtained as a light yellow oil.

EXAMPLE 9

1-(4-Fluorophenyl)-2-(1H-imidazol-1-yl)-N-(phenylmethyl)ethanimine N-oxide (2, $R^1$=4-$FC_6H_4$, $R^2$=$C_6H_5$, X=CH)

Compound 2 ($R^1$=4-$FC_6H_4$, $R^2$=$C_6H_5$, X=CH) was prepared by the procedure described in Example 1, Method B, by reacting 2-(1H-imidazol-1-yl)-4'-fluoroacetophenone (1, $R^1$=4-$FC_6H_4$, X=CH) with N-benzylhydroxylamine. Compound 2 ($R^1$=4-$FC_6H_4$, $R^2$=$C_6H_5$, X=CH) was obtained as a light yellow oil.

EXAMPLE 10

N-Methyl-1-phenyl-2-(1H-1,2,4-triazol-1-yl)ethanimine N-oxide (2, $R^1$=$C_6H_5$, $R^2$=H, X=N) was prepared by the procedure described in Example 1, Method A, by reacting 2-(1H-1,2,4-triazol-1-yl) acetophenone (1, $R^1$=$C_6H_5$, X=N) with N-methylhydroxylamine hydrochloride. Compound 2 ($R^1$=$C_6H_5$, $R^2$=H, X=N) has a melting point of 117°–119° C. (ethyl acetate).

EXAMPLE 11

1-(4-Chlorophenyl)-N-methyl-2-(1H-1,2,4-triazol-1-yl)ethanimine N-oxide (2, $R^1$=4-$ClC_6H_4$, $R^2$=H, X=N)

Compound 2 ($R^1$=4-$ClC_6H_4$, $R^2$=H, X=N) was prepared by the procedure described in Example 1, Method A by reacting 2-(1H-1,2,4-triazol-1-yl)-4'-chloroacetophenone (1, $R^1$=4-$ClC_6H_4$, X=N) with N-methylhydroxylamine hydrochloride. Compound 2 ($R^1$=4-$ClC_6H_4$, $R^2$=H, X=N) has a melting point of 119°–121° C. (ethyl acetate). Anal. Calcd for $C_{11}H_{11}ClN_4O$: C, 52.70; H, 4.42; N, 22.35; Cl, 14.14. Found: C, 52.65; H, 4.44; N, 22.37; Cl, 13.93.

EXAMPLE 12

1-(4-Methoxyphenyl)-N-methyl-2-(1H-1,2,4-triazol-1-yl)ethanimine N-oxide (2, $R^1$=4-$CH_3OC_6H_4$, $R^2$=H, X=N)

Compound 2 ($R^1$=4-$CH_3OC_6H_4$, $R^2$=H, X=N) was prepared by the procedure described in Example 1, Method A, by reacting 2-(1H-1,2,4-triazol-1-yl)-4'-methoxyacetophenone (1, $R^1$=4-$CH_3OC_6H_4$, X=N) with N-methylhydroxylamine hydrochloride. Compound 2 ($R^1$=4-$CH_3OC_6H_4$, $R^2$=H, X=N) has a melting point of 128°–121° C. (ethyl acetate). Anal. Calcd for $C_{12}H_{14}N_4O$: C, 58.53; H, 5.73; N, 22.75. Found: C, 58.61; H, 5.76; N, 22.86.

EXAMPLE 13

1-(4-Fluorophenyl)-N-methyl-2-(1H-1,2,4-triazol-1-yl)ethanimine N-oxide (2, $R^1$=4-$FC_6H_4$, $R^2$=H, X=N)

Compound 2 ($R^1$=4-$FC_6H_4$, $R^2$=H, X=N) was prepared by the procedure described in Example 1, Method A, by reacting 2-(1H-1,2,4-triazol-1-yl)-4'-fluoroacetophenone (1, $R^1$=4-$FC_6H_4$, X=N) with N-methylhydroxylamine hydrochloride. Compound 2 ($R^1$=4-$FC_6H_4$, $R^2$=H, X=N) was obtained as a light yellow oil.

EXAMPLE 14

N-Methyl-1-(3-methylphenyl)-2-(1H-1,2,4-triazol-1-yl)ethanimine N-oxide (2, $R^1$=3-$CH_3C_6H_4$, $R^2$=H, X=N)

Compound 2 ($R^1$=3-$CH_3C_6H_4$, $R^2$=H=N) was prepared by the procedure described in Example 1, Method B, by reacting 2-(1H-1,2,4-triazol-1-yl)-3'-methylacetophenone (1, $R^1$=3-$CH_3C_6H_4$, X=N) with N-methylhydroxylamine hydrochloride. Compound 2 ($R^1$=3-$CH_3C_6H_4$, $R^2$=H, X=N) has a melting point of 98°-100° C. (ethyl acetate).

EXAMPLE 15

2-(1H-Imidazol-1-yl)-N-methyl-1-(2-naphthyl)ethanimine N-oxide (2, $R^1$=2-$C_{10}H_7$, $R^2$=H, X=CH)

Compound 2 ($R^1$=2-$C_{10}H_7$, $R^2$=H, X=N) was prepared by the procedures described in Example 1, Method A and B, by reacting 2-(1H-imidazol-1-yl)-1-(2-naphthyl)ethanone (1, $R^1$=2-$C_{10}H_7$, X=CH) with N-methylhydroxylamine hydrochloride. Compound 2 ($R^1$=2-$C_{10}H_7$, $R^2$=H, X=CH) has a melting point of 112°-114° C. (ethyl acetate). Anal. Calcd for $C_{16}H_{15}N_3O$: C, 72.43; H, 5.70; N, 15.84. Found: (method A prep.) C, 72.14; H, 5.79; N, 15.74.

EXAMPLE 16

1-(2-Furanyl)-2-(1H-imidazol-1-yl)-N-methylethanimine N-oxide (2, $R^1$=2-$C_4H_3O$, $R^2$=H, X=CH)

Compound 2 ($R^1$=2-$C_4H_3O$, $R^2$32 H, X=CH) was prepared by the procedure described in Example 1, Method B, by reacting 1-(2-furanyl)-2-(1H-imidazol-1-yl)ethanone (1, $R^1$=2-$C_4H_3O$, X=CH) with N-methylhydroxylamine hydrochloride. Compound 2 ($R^1$=2-$C_4H_3O$, $R^2$=H, X=CH) has a melting point of 130°-133° C. (ethyl acetate). Anal. Calcd for $C_{10}H_{11}N_3O$: C, 58.53, H, 5.40; N, 20.48. Found: C, 58.60; H, 5.47; N. 20.49.

EXAMPLE 17

2-(1H-Imidazol-1-yl)-N-methyl-1-(2-thienyl)ethanimine N-oxide (2, $R^1$=3-$C_4H_3S$, $R^2$=H, X=CH)

Compound 2 ($R^1$=2-$C_4H_3S$, $R^2$=H, X=CH) was prepared by the procedure described in Example 1, Method B, by reacting 2-(1H-imidazol-1-yl)-1-(2-thienyl)ethanone (1, $R^1$=2-$C_4H_3S$, X=CH) with N-methylhydroxylamine hydrochloride. Compound 2 ($R^1$=2-$C_4H_3S$, $R^2$=H, X=CH) has a melting point of 162°-164° C. (ethyl acetate).

The compounds of this invention are useful intermediates for the preparation of substituted isoxazolidine derivatives having antifungal activity. Examples of such derivatives are disclosed, for example, in our concurrently filed copending applications entitled "Substituted 5-(Phenoxyalkyl)-3-phenyl-3-(1H-imidazol-1-ylmethyl)-2-methylisoxazolidines"; "Substituted 3,5-Diphenyl-3-(1H-imidazol-1-ylmethyl)-2-methylisoxazolidines" (U.S. Pat. No. 4,719,306), "3-(Substituted phenyl)-3-(1H-imidazol-1-ylmethyl)-2-methyl-5-{[(substituted phenyl)thio]methyl}isoxazolidine" Derivatives; and "3-(Substituted phenyl)-3-(1H-1,2,4-triazol-1-yl)methyl-2-methyl-5-[(substituted phenoxy)methyl]isoxazolidine Derivatives" whose disclosures are incorporated by reference herein.

The substituted isoxazolidines are prepared by reacting the compounds of the invention with an appropriate allyl benzene, allyl phenyl ether or allyl phenyl sulfide compound to provide the desired isoxazolidines. For example, 5-(4-chlorophenoxymethyl)-3-phenyl-3-(1H-imidazol-1-ylmethyl)-2-methylisoxazolidine can be prepared by reacting the compound of Example 1 with 4-chlorophenyl allyl ether in refluxing toluene in a nitrogen atmosphere for about 40 hours. Other compounds of the invention can be used to prepare corresponding isoxazolidines in a similar manner. The isoxazolidines have been determined to have in vitro antifungal activity against yeast and systemic mycoses and dermatophytes as determined by broth and agar testing techniques [(McGinnis, M. R., *Laboratory Handbook of Medical Mycology*, Academic Press, N.Y., N.Y. (1980)].

We claim:

1. A compound of the formula:

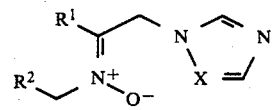

wherein;

$R^1$ is selected from 2-naphthyl, 2-furanyl, 2-thienyl, phenyl, and substituted phenyl having one or more of the meta and para hydrogens substituted by halogen, lower alkyl, lower alkoxy, or combinations thereof, $R^2$ is selected from hydrogen and phenyl, and X is a methyn group.

2. The compound of claim 1 wherein $R^1$ is phenyl or substituted phenyl, $R^2$ is hydrogen, and X is methyn.

3. The compound of claim 2 wherein the compound is 2-(1H-imidazol-1-yl)-N-methyl-1-phenylethanimine N-oxide.

4. The compound of claim 2 wherein the compound is 1-(4-chlorophenyl)-2-(1H-imidazol-1-yl)-N-methylethanimine N-oxide.

5. The compound of claim 2 wherein the compound is 1-(4-fluorophenyl)-2-(1H-imidazol-1-yl)-N-methylethanimine N-oxide.

6. The compound of claim 2 wherein the compound is 2-(1H-imidazol-1-yl)-1-(4-methoxyphenyl)-N-methylethanimine N-oxide.

7. The compound of claim 2 wherein the compound is 2-(1H-imidazol-1-yl)-1-(3-methoxyphenyl)-N-methylethanimine N-oxide.

8. The compound of claim 2 wherein the compound is 2-(1H-imidazol-1-yl)-N-methyl-1-(3-methylphenyl)ethanimine N-oxide.

9. The compound of claim 2 wherein the compound is 1-(4-chloro-3-methylphenyl)-2-(1H-imidazol-1-yl)-N-methylethanimine N-oxide.

10. The compound of claim 1 wherein $R^1$ is phenyl or substituted phenyl, $R_2$ is phenyl, and X is methyn.

11. The compound of claim 10 wherein the compound is 2-(1H-imidazol-1-yl)-1-phenyl-N-(phenylmethyl)ethanimine N-oxide.

12. The compound of claim 10 wherein the compound is 1-(4-fluorophenyl)-2-(1H-imidazol-1-yl)-N-(phenylmethyl)ethanimine N-oxide.

13. The compound of claim 1 wherein $R^1$ is 2-naphthyl, $R^2$ is hydrogen and X is methyn.

14. The compound of claim 13 wherein the compound is 2-(1H-imidazol-1-yl)-N-methyl-1-(2-naphthyl)ethanimine N-oxide.

15. The compound of claim 1 wherein $R^1$ is 2-furanyl, $R^2$ is hydrogen and X is methyn.

16. The compound of claim 5 wherein the compound is 1-(2-furanyl)-2-(1H-imidazol-1-yl)-N-methylethanimine N-oxide.

17. The compound of claim 1 wherein $R^1$ is 2-thienyl, $R^2$ is hydrogen and X is methyn.

18. The compound of claim 17 wherein the compound is 2-(1H-imidazol-1-yl)-N-methyl-1-(2-thienyl)ethanimine N-oxide.

* * * * *